(12) United States Patent
Pan

(10) Patent No.: US 6,324,242 B1
(45) Date of Patent: Nov. 27, 2001

(54) FAST RECONSTRUCTION WITH UNIFORM NOISE PROPERTIES IN HALF-SCAN TOMOGRAPHY

(75) Inventor: Xiaochuan Pan, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/503,609

(22) Filed: Feb. 11, 2000

Related U.S. Application Data

(63) Continuation-in-part of application No. 09/289,297, filed on Apr. 9, 1999.

(51) Int. Cl.[7] ........................................... A61B 6/03
(52) U.S. Cl. ................................... 378/4; 378/901
(58) Field of Search .............................. 378/4, 15, 901

(56) References Cited

U.S. PATENT DOCUMENTS

| | | | |
|---|---|---|---|
| 5,216,601 | * | 6/1993 | Crawford et al. ............... 378/14 |
| 5,233,518 | * | 8/1993 | King et al. ..................... 378/14 |
| 5,270,923 | * | 12/1993 | King et al. ..................... 382/131 |
| 5,559,847 | * | 9/1996 | Hu et al. ........................ 378/4 |

* cited by examiner

Primary Examiner—David V. Bruce
(74) Attorney, Agent, or Firm—Welsh & Katz, Ltd.

(57) ABSTRACT

A method and apparatus are provided for reconstructing a tomographic image from a halfscan fan-beam sinogram using the parallel beam reconstruction algorithms. The method includes the steps of weighting at least some elements of the halfscan fan-beam sinogram to forming a weighted fan-beam sinogram and expanding the weighted fan-beam sinogram into a Fourier series. The method further includes the steps of linearly interpolating at least some elements of the Fourier series to form a parallel beam sinogram of linearly interpolated data and reconstructing the image from the parallel beam sinogram using the parallel beam reconstruction algorithms.

25 Claims, 4 Drawing Sheets

FAST RECONSTRUCTION WITH UNIFORM NOISE PROPERTIES IN HALF-SCAN TOMOGRAPHY

This application is a continuation-in-part of U.S. patent application Ser. No. 09/289,297, filed on Apr. 9, 1999 and assigned to the assignee of the present invention.

The U.S. Government has a paid-up license in this invention and the right in limited circumstances to require the patent owner to license others on reasonable terms as provided for by the terms of Grant #R29CA70449 as awarded by the National Institute of Health.

FIELD OF THE INVENTION

The field of the invention relates to computer tomography and more particularly to the reconstruction of images from fan-beam sinograms.

BACKGROUND OF THE INVENTION

In tomographic imaging, a finite set of imaging samples are obtained of the underlying multi-dimensional function of interest. However, because of various physical restrictions of the sampling system, these samples are often obtained on nonuniform grids, thereby preventing the direct use and meaningful interpretation of these data. For example, in medical tomographic imaging such as the two-dimensional (2D) fan-beam computed tomography (CT), single-photon emission computed tomography (SPECT), positron emission tomography (PET), spiral (or helical) CT, diffraction tomography (DT), and magnetic resonance imaging (MRI), the acquired data are often sampled on nonuniform grids in the sinogram space, thus preventing the direct use of existing methods that are computationally efficient and numerically stable for reconstruction of tomographic images. In these situations, one can always use various multi-dimensional interpolation (MDI) methods to convert the samples that lie on nonuniform grids into samples that lie on uniform grids so that they can be processed directly and be presented meaningfully.

A wide variety of MDI methods have previously been developed. The methods that are based upon the Whittaker-Shannon sampling (WST) theorem can potentially provide accurate interpolation results. Unfortunately, these methods generally possesses the shortcoming of great computational burden, which increases drastically as the number of interpolation dimensions increases ("the curse of the dimensionality"). Attempts have been made to alleviate the computational burden by developing efficient interpolation methods. However, these methods are all associated with certain approximations. Virtually all of the previously developed methods calculate the desired uniform samples directly from the measured nonuniform samples, which generally requires the use of computationally burdensome algorithms if accuracy is to be preserved.

SUMMARY

A method and apparatus are provided for reconstructing a tomographic image from a halfscan fan-beam sinogram using the parallel beam reconstruction algorithms. The method includes the steps of weighting at least some elements of the halfscan fan-beam sinogram to forming a weighted fan-beam sinogram and expanding the weighted fan-beam sinogram into a Fourier series. The method further includes the steps of linearly interpolating at least some elements of the Fourier series to form a parallel beam sinogram of linearly interpolated data and reconstructing the image from the parallel beam sinogram using the parallel beam reconstruction algorithm.

DETAILED DESCRIPTION OF A PREFERRED EMBODIMENT

Figure 1:
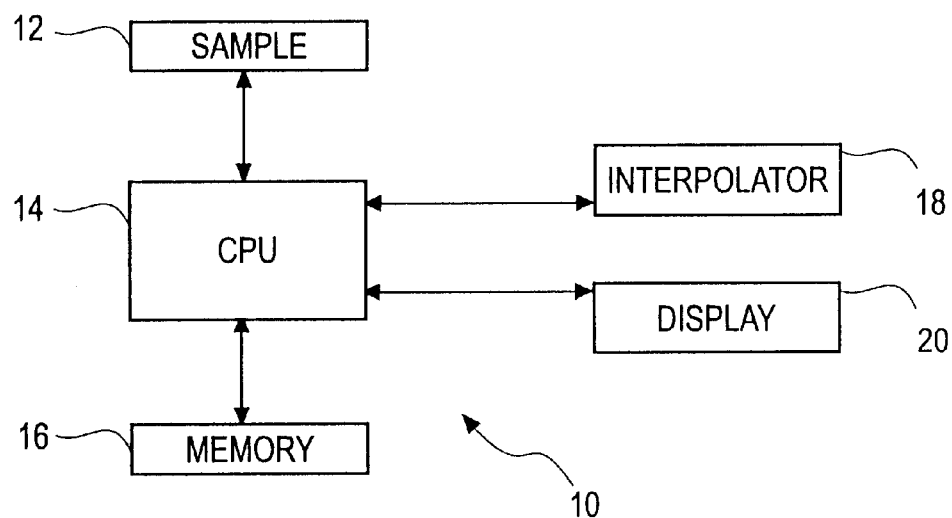
FIG. 1 depicts an system for reconstructing images in accordance with an illustrated embodiment of the invention.
Figure 2:
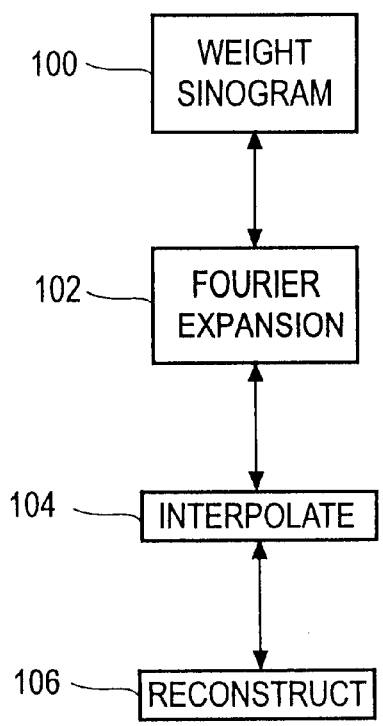
FIG. 2 depicts a flow chart of method steps that may be used by the system of FIG. 1.

FIG. 1 is a half-scan imaging system 10, generally in accordance with an illustrated embodiment of the invention. FIG. 2 is a flow chart of processing steps that may be used by the structure of FIG. 1 to generate images from half-scan fan-beam sinograms.

Under the illustrated embodiment, a sampling device 12 acquires samples 100 under an appropriate format (e.g., halfscan fan-beam CT) under the control of a central processing unit (CPU) 14. The CPU 14 may store the samples in a memory unit 16 or process the samples directly.

In general, conventional interpolation techniques calculate a function by directly using its measured samples. However, because the values of a function can readily be calculated from its Fourier transform (FT), the interpolation task could be compared to estimating the FT of a function from its measured samples. Based upon this observation, an approach is provided for reducing the interpolation dimensions in MDI problems.

Let $f(\vec{x}_1, \vec{x}_2)$ and $g(\vec{y}_1, \vec{y}_2)$ be K-dimensional (KD) band-limited functions, where $\vec{x}_1=(x_1, x_2 \ldots x_k)^T$ and $\vec{y}_1=(y_1, y_2 \ldots y_k)^T$ are kD vectors, $\vec{x}_2=(x_{k+1}, x_{k+2} \ldots x_K)^T$ and $\vec{y}_2=(y_{k+1}, y_{k+2} \ldots y_K)^T$ are MD vectors, and K=M+k and K>k. Suppose that $f(\vec{x}_1, \vec{x}_2)=g(\vec{y}_1, \vec{y}_2)$ mathematically. Because the transformation between the $\{\vec{x}_1, \vec{x}_2\}$ and $\{\vec{y}_1, \vec{y}_2\}$ spaces can be generally non-linear, uniform samples of $g(\vec{y}_1, \vec{y}_2)$ in the $\{\vec{y}_1, \vec{y}_2\}$ space produce generally non-uniform samples of $f(\vec{x}_1, \vec{x}_2)$ in the $\{\vec{x}_1, \vec{x}_2\}$ space. The MDI task is to estimate uniform samples of $f(\vec{x}_1, \vec{x}_2)$ in the $\{\vec{x}_1, \vec{x}_2\}$ space from a set of measured uniform samples of $g(\vec{y}_1, \vec{y}_2)$ in the $\{\vec{y}_1, \vec{x}_2\}$ space, where the sampling rate satisfies the Nyquist conditions. In a wide class of MDI problems such as those that arise in medical imaging, the transformation between the $\{\vec{x}_1, \vec{x}_2\}$ and $\{\vec{y}_1, \vec{y}_2\}$ spaces has a general form, given by $$\vec{x}_1 = \vec{h}_1(\vec{y}_1) \tag{1a}$$

$$\vec{x}_2 = \vec{h}_2(\vec{y}_1, \vec{y}_2) = a\vec{y}_2 + \vec{b}(\vec{y}_1), \tag{1b}$$

where $\vec{h}_2$ denotes a general linear transformation (LT) between the $\{\vec{x}_2\}$ and $\{\vec{y}_2\}$ subspaces, whereas $\vec{h}_1$ denotes a general non-LT between the $\{\vec{x}_1\}$ and $\{\vec{y}_1\}$ subspaces. The known matrix a is independent of $\vec{y}_1$ and $\vec{y}_2$, and the known vector $\vec{b}$ can be any real or complex function of $\vec{y}_1$. The known matrix a and vector $\vec{b}$ represent transfer functions (i.e., a set of relationships) which relate the first set of samples $f(\vec{x}_1, \vec{x}_2)$ to the second set of samples $g(\vec{y}_1, \vec{y}_2)$ (i.e., the two sampling spaces) in a known manner.

Let $F(\vec{x}_1, \vec{v}_{\vec{x}2})$ and $G(\vec{y}_1, \vec{v}_{\vec{y}2})$ be the partial FTs of $f(\vec{x}_1, \vec{x}_2)$ and $g(\vec{y}_1, \vec{y}_2)$ with respect to $\vec{x}_2$ and $\vec{y}_2$, respectively, where $\vec{v}_{\vec{x}2}$ and $\vec{v}_{\vec{y}2}$ denote the corresponding frequencies of $\vec{x}_2$ and $\vec{y}_2$. It can be shown that $$F(\vec{x}_1, \vec{v}_{\vec{x}2}) = \|a\| G(\vec{y}_1, a^T \vec{v}_{\vec{x}2}) e^{-j2\pi \vec{v}_{\vec{x}2} \cdot \vec{b}(\vec{y}_1)}, \tag{2}$$

where $\|a\|$ and $a^T$ are the determinant and transpose of a. Because $G(\vec{y}_1, \vec{v}_{\vec{y}2})$ can readily be obtained with the fast FT (FFT) from the measured samples of $g(\vec{y}_1, \vec{y}_2)$ in $\{\vec{y}_2\}$ subspace, one can calculate $F(\vec{x}_1, \vec{v}_{\vec{x}2})$ by using Eqn. (2) and then $f(\vec{x}_1, \vec{x}_2)$ in the $\{\vec{x}_2\}$ subspace by invoking the inverse FFT. Therefore, the CPU 14 accomplishes the interpolation task in the $\{\vec{x}_2\}$ subspace and effectively reduces the original KD interpolation task of Eqn. (1) to a kD one between the $\{\vec{x}_1\}$ and $\{\vec{y}_1\}$ subspaces.

For another class of MDI problems, the transformation between the $\{\vec{x}_1\}$ and $\{\vec{y}_1\}$ subspaces is described by Eqn. (1a), whereas the transformation between the $\{\vec{x}_2\}$ and $\{\vec{y}_2\}$ subspaces is given by $$x_{k+i} = c_i y_{k+i} + b_i(\vec{y}_1, y_{k+1}, y_{k+2}, \ldots, y_{k+i-1}), \tag{3}$$

where $x_{k+i}$, $y_{k+i}$, $b_i$ and $c_i$ are the components of $\vec{x}_2$, $\vec{y}_2$, $\vec{b}$ and $\vec{c}$, $i=1, 2 \ldots M$. We assume that the vectors $\vec{b}$ and $\vec{c}$ are known. It should be noted that $\vec{b}$ in Eqn. (1b) is completely independent of $\vec{y}_2$, whereas $\vec{b}$ in Eqn. (3) can be a general non-linear function of the components of $\vec{y}_2$. One can show that $F(\vec{x}_1, \vec{v}_{\vec{x}2})$ can be expressed as $$F(\vec{x}_1, v_{k+1}, v_{k+2} \ldots v_{k+M}) = c_1 e^{-j2\pi v_{k+1} b_1(} \\ \vec{y}_1) \times \int dy_{k+1} e^{-j2\pi c_1 v_{k+1} y_{k+1}} G^{(M-1)}(\vec{y}_1, y_{k+1}, v_{k+2} \ldots v_{k+M}) \tag{4}$$

where $\vec{v}_{\vec{x}2} = (v_{k+1}, v_{k+2} \ldots v_{k+M})^T$, and $$G^{(i)}(\vec{y}_1, y_{k+1} \ldots y_{k+M-i}, v_{k+M-i+1} \ldots v_{k+M})$$
$$= c_{M-i+1} e^{-j2\pi v_{k+M-i+1} b_{M+1-i}(\vec{y}_1, y_{k+1} \ldots y_{k+M-i})}$$
$$\times \int dy_{k+M-i} e^{-j2\pi c_{M-i+1} v_{k+M-i+1} y_{k+M-i+1}} G^{(i-1)}(\vec{y}_1,$$
$$y_{k+1} \ldots y_{k+M-i}, y_{k+M-i+1}, v_{k+M-i+2} \ldots v_{k+M}) \tag{5}$$

with $G^{(0)}(\vec{y}_1, y_{k+1} \ldots y_{k+M}) = g(\vec{y}_1, \vec{y}_2)$ and $i=1, 2 \ldots M-1$. The integrals in Eqns. (4) and (5) denote 1D FTs that can be calculated by invoking the 1D FFT. Using Eqns. (4) and (5), the CPU 14 can calculate $F(\vec{x}_1, \vec{v}_{\vec{x}2})$ from knowledge of $g(\vec{y}_1, \vec{y}_2)$ in the $\{\vec{y}_2\}$ subspace. From $F(\vec{x}_1, \vec{v}_{\vec{x}2})$, the CPU 14 can obtain $f(\vec{x}_1, \vec{x}_2)$ by invoking the inverse FFT and thus accomplish the interpolation task in the $\{\vec{x}_2\}$ subspace. Therefore, the original KD interpolation task of Eqns. (1a) and (3) is thus reduced effectively to a kD one between the $\{\vec{x}_1\}$ and $\{\vec{y}_1\}$ subspaces.

In fan-beam CT, one can measure uniform samples of $g(\alpha, \beta)$ in the $\{\alpha, \beta\}$ space. Reconstruction of a CT image requires uniform samples of $f(\xi, \phi)$ in the $\{\xi, \phi\}$ space. One can show that $f(\xi, \phi) = g(\alpha, \beta)$, provided $$\xi = F \sin\alpha \tag{6a}$$

$$\phi = \beta + \alpha, \tag{6b}$$

where F is the focal length of the fan-beam system. Because the transformation in Eqn. (6) is non-linear, a 2D interpolation may be used to calculate uniform samples of $f(\xi, \phi)$ in the $\{\xi, \phi\}$ space from that of $g(\alpha, \beta)$ in the $\{\alpha, \beta\}$ space. However, comparison of Eqns. (6b) and (1b) indicates that $\phi$ is a 1D LT of $\beta$ with a=1 and b=$\alpha$ and that the interpolation between the $\{\phi\}$ and $\{\beta\}$ subspaces can thus be accomplished by using Eqn. (2). Hence, the 2D interpolation task in 2D fan-beam CT is reduced effectively to a 1D interpolation task between the $\{\xi\}$ and $\{\alpha\}$ subspaces.

The use of the multidimensional interpolation discussed above allows for the development and use of hybrid algorithms for the reconstruction of CT images. As used herein a hybrid algorithm is a method of reconstruction that relies upon the multidimensional interpolation method set forth above as a method of substantially simplifying image reconstruction.

Hybrid algorithms inherently possess computational and noise properties superior to those of the fan-beam filtered backprojection (FFBP) algorithm. However, the hybrid algorithms cannot be applied directly to a halfscan fan-beam sinogram because they require knowledge of a fullscan fan-beam sinogram. In the following description, halfscan-hybrid algorithms are described which can be used for image reconstruction in halfscan CT.

Numerical evaluation indicates that the proposed halfscan-hybrid algorithms are computationally more efficient than are the widely used halfscan-FFBP algorithms. More important, the results of quantitative studies demonstrate clearly that the noise levels in images reconstructed by use of the halfscan-hybrid algorithm are generally lower and spatially much more uniform than are those in images reconstructed by use of the halfscan-FFBP algorithm. Such reduced and uniform image noise levels may be translated into improvement of the accuracy and precision of lesion detection and parameter estimation in noisy CT images without increasing the radiation dose to the patient. Therefore, the halfscan-hybrid algorithms have significant implication for image reconstruction in conventional CT and, in particular, helical CT.

The widely used fan-beam filtered backprojection (FFBP) algorithm in computed tomography (CT) reconstructs an image directly from the fan-beam sinogram. Alternatively, the hybrid algorithms estimate the parallel-beam sinogram from the fan-beam sinogram without an explicit interpolation between the fan-beam and parallel-beam projection angles and then reconstruct the image by use of parallel-beam reconstruction algorithms such as the filtered back-projection (FBP) algorithm. The hybrid algorithms possess several potential advantages over the FFBP algorithm: the former are computationally more efficient than is the latter; and the noise levels in images reconstructed by use of the former are significantly lower and much more uniform than those in images reconstructed by use of the latter. Low and uniform noise levels in CT images are always desirable because they may improve the accuracy of estimation of parameters of interest and the detection of subtle signals in noisy images It is possible to reduce the scanning time and radiation dose in CT imaging by use of the so-called halfscan approach, in which one acquires the halfscan fan-beam sinogram at projection angles from zero to r plus the fan angle. Other investigators have proposed the halfscan-FFBP algorithms, which first weighted the halfscan fan-beam sinogram and then applied the FFBP algorithm to reconstruct the image. However, because of their use of the FFBP algorithm, the halfscan-FFBP algorithms suffer from computational and noise problems similar to those that plague the FFBP algorithm. Additionally, although the noise properties in parallel-beam and fullscan fan-beam CT have been investigated previously, there is a lack of analysis of the noise and numerical properties of image reconstruction in halfscan CT.

The hybrid algorithms cannot be applied directly to the halfscan fan-beam sinogram because they require knowledge of the full scan sinogram at projection angles from zero to $2\pi$. Because of the potential advantages of the hybrid algorithms, however, it is theoretically interesting and practically important to generalize them to the halfscan situation. In this work, halfscan-hybrid algorithms are developed for image reconstruction in halfscan CT. The noise and numerical properties of the halfscan-hybrid and the widely used halfscan-FFBP algorithms are also developed and compared, demonstrating that the halfscan-hybrid algorithms possess properties similar to those of fullscan hybrid algorithms, and, more importantly, possess computational and noise properties superior to those of the halfscan-FFBP algorithms.

The description in the following sections is organized as follows. In the following section, the necessary notation and equations are introduced by summarizing the hybrid algorithms and the halfscan-FFBP algorithms. In the section after that, the halfscan-hybrid algorithms are developed. In the next following section, we describe numerical studies for evaluation and comparison of the halfscan-FFBP and halfscan-hybrid algorithms. In the final section, we present a discussion of the work.

We first consider the theoretical background. Let $a(r,\theta)$ denote a two dimensional (2D) image, where r and $\theta$ are the polar coordinates. Also, let $p(\xi,\phi)$ denote the parallel-beam sinogram of $a(r,\theta)$, where $\xi$ and $\phi$ represent the detector-bin indices and projection angles, respectively. From knowledge of $p(\xi,\phi)$, one can reconstruct $a(r,\theta)$ by use of a variety of reconstruction algorithms such as the FBP algorithm, which can be expressed as $$a(r,\theta) = \int_{\phi=0}^{2\pi}\int_{\xi=-\infty}^{\infty}\sum_{k=-\infty}^{\infty} P_k(\xi)e^{jk\phi}h(r\cos(\phi-\theta)-\xi)d\xi d\phi, \quad (7)$$

where $h(\xi)$ is the inverse Fourier transform of the ramp filter, $P_k(\xi)$ is the Fourier series expansion of $p(\xi,\phi)$ with respect to $\phi$, and $k=0, \pm 1, \pm 2 \ldots$ is the angular frequency index.

The Fan-Beam Filtered Backprojection (FFBP) Algorithm will be considered next. Let $q(\alpha,\beta)$ denote the fan-beam sinogram of the image $a(r,\theta)$, where $\alpha$ and $\beta$ represent the detector-bin indices and projection angles in the fan-beam projection configuration. In a fullscan situation, one acquires the fullscan fan-beam $q(\alpha,\beta)$ in the complete data space $W=[|\alpha|\leq\alpha_m, 0\leq\beta\leq 2\pi]$, where $\alpha_m>0$ is the maximum open angle of the curved detector array in a CT system such that $q(\alpha,\beta)=0$ for $\alpha>\alpha_m$. A well-known relationship between the parallel-beam sinogram $p(\xi,\phi)$ and the fan-beam sinogram $q(\alpha,\beta)$ is given by $$p(\xi,\phi)=q(\alpha,\beta) \quad (8)$$

where $$\xi=F\sin\alpha \text{ and } \phi=\beta+\alpha \quad (9)$$

and F is the focal length of the fan-beam system.

Using Eqs. (8) and (9) in Eq. (7), one can readily derive the FFBP algorithm that reconstructs the image directly from the fullscan fan-beam sinogram $q(\alpha,\beta)$. Mathematically, the FFBP algorithm can be expressed as $$a(r,\theta) = \frac{1}{2}\int_{\beta=0}^{2\pi}\frac{F}{L^2} \quad (10)$$

$$\int_{\alpha=-\alpha_m}^{\alpha_m} q(\alpha,\beta)\left[\frac{(\alpha_0-\alpha)}{\sin(\alpha_0-\alpha)}\right]^2 \cos\alpha h(\alpha_0-\alpha)d\alpha d\beta,$$

where $L = \{[F+r\sin(\beta-\theta)]^2+[r\cos(\beta-\theta)]^2\}^{\frac{1}{2}}$ and $$\alpha_0 = \arctan\left[\frac{r\cos(\beta-\theta)}{F+r\sin(\beta-\theta)}\right].$$

Hybrid algorithms will be considered next. As an alternative to the FFBP algorithm, hybrid algorithms have been proposed for image reconstruction from a fullscan fan-beam sinogram. Let $Q_k(\alpha)$ denote the Fourier series expansion of the fullscan fan-beam sinogram $q(\alpha,\beta)$ with respect to $\beta$, i.e., $$Q_k(\alpha) = \frac{1}{2\pi} \int_{\beta=0}^{2\pi} q(\alpha, \beta) e^{-jk\beta} d\beta. \quad (11)$$

where $|\alpha| \leq \alpha_m$, and the angular frequency index $k=0, \pm 1, \pm 2 \ldots$ Using Eq. (11), one can readily obtain $Q_k(\alpha)$ from the fullscan fan-beam sinogram $q(\alpha,\beta)$.

The hybrid algorithm first estimates $P_k(\xi)$ (i.e., the parallel-beam sinogram) from $Q_k(\alpha)$ (i.e., the fullscan fan-beam sinogram):

$$P_k(\xi) = \omega(\alpha,k)\gamma^k Q_k(\alpha) + (1-\omega(\alpha,k))(-1)^k \gamma^{-k} Q_k(-\alpha) \quad (12)$$

where $\xi \geq 0$, $k=0, \pm 1, \pm 2 \ldots$, $\gamma = e^{-j\alpha}$, and $\omega(\alpha,k)$ is the combination coefficient that can be a general complex function of $\alpha$ and $k$. From the estimated $P_k(\xi)$, the hybrid algorithm subsequently reconstructs the image $a(r,\theta)$ by use of computationally efficient and numerically stable algorithms such as the FBP algorithm in Eq. (7). Different choices of $\omega(\alpha,k)$ specify different hybrid algorithms. It was observed theoretically and demonstrated quantitatively that, because the ratio F/L in the FFBP algorithm (see Eq. (10)) is spatially variant (i.e., a function of r, θ, and β) and can be larger than 1, the FFBP algorithm is computationally less efficient and more susceptible to the effects of data noise and sample aliasing than are the hybrid algorithms.

The halfscan algorithms will be considered next. One can divide the complete dataspace W into four subspaces A, B, C, and D, where $A=[|\alpha| \leq \alpha_m, 0 \leq \beta < 2\alpha_m - 2\alpha]$, $B=[|\alpha| \leq \alpha_m, 2\alpha_m - 2\alpha < \beta \leq \pi - 2\alpha]$, $C=[|\alpha| \leq \alpha_m, \pi - 2\alpha \leq \beta < \pi + 2\alpha_m]$, and $D=[|\alpha| \leq \alpha_m, \pi + 2\alpha_m \leq \beta < 2\pi]$. In a halfscan situation, $q(\alpha,\beta)$ is obtained only in the subspace $H = A \cup B \cup C = [|\alpha| \leq \alpha_m, 0 \leq \beta \leq \pi + 2\alpha_m]$, which is referred to as a halfscan fan-beam sinogram. Although this halfscan fan-beam sinogram contains all of the information necessary for reconstruction of the image, it also includes partially redundant information in subspaces A and C which, without being adequately normalized, can result in image artifacts. The halfscan-FFBP algorithm first normalizes such partially redundant information by generating an appropriately weighted fan-beam sinogram $q'(\alpha,\beta)$ and then uses the FFBP algorithm of Eq. (10) for exact reconstruction of the image. The appropriately weighted fan-beam sinogram $q'(\alpha,\beta)$ is given by $$q'(\alpha,\beta) = q(\alpha,\beta)\omega(\alpha,\beta) \quad (13)$$

where the weighting function $\omega(\alpha,\beta)$ satisfies $$\omega(\alpha,\beta) + \omega(-\alpha,\beta+2\alpha+\pi) = 1 \quad (14)$$

for $(\alpha,\beta)$ in the complete space M, $\omega(\alpha,\beta)=1$ for $(\alpha,\beta)$ in subspace B, and $\omega(\alpha,\beta)=0$ for $(\alpha,\beta)$ in subspace D. Although the forms of $\omega(\alpha,\beta)$ for $(\alpha,\beta)$ in subspaces B and D are completely specified, explicit forms of $\omega(\alpha,\beta)$ for $(\alpha,\beta)$ in subspaces A and C are unspecified so far. In principle, one can design different halfscan-FFBP algorithms by choosing different $\omega(\alpha,\beta)$ for $(\alpha,\beta)$ in subspaces A and C as long as they satisfy Eq. (14). The reconstructions obtained using different choices of $\omega(\alpha,\beta)$ will respond differently to the effects of data noise and sample aliasing Halfscan-hybrid algorithms will be discussed next. Because the halfscan-FFBP algorithms use the FFBP algorithm for image reconstruction from the weighted sinograms $q'(\alpha,\beta)$, they are expected to be less computationally efficient and more susceptible to the effects of data noise and sample aliasing than are the hybrid algorithms described above. However, these hybrid algorithms cannot be applied directly to the halfscan fan-beam sinogram because they estimate $P_k(\xi)$ from $Q_k(\alpha)$ in Eq. (12), the calculation of which in Eq. (11) requires knowledge of the fullscan fan-beam sinogram for $0 \leq \beta < 2\pi$.

The derivation of the halfscan-hybrid algorithms will be considered next. In the discussion below, we develop halfscan-hybrid algorithms that can be applied to the halfscan fan-beam sinogram and that possess computational and noise properties similar to those of the hybrid algorithms. Using $q'(\alpha,\beta)$ of Eq. (13) in Eq. (10), the halfscan-FFBP algorithm can be rewritten as $$a(r,\theta) = \int_{\beta=0}^{2\pi} \frac{F}{L^2} \int_{\alpha=0}^{\alpha_m} [q'(\alpha,\beta) + q'(-\alpha,\beta+\pi)] \left[\frac{(\alpha_0 - \alpha)}{\sin(\alpha_0 - \alpha)}\right]^2 \quad (15)$$
$$\cos\alpha h(\alpha_0 - \alpha) d\alpha d\beta.$$

Using Eq. (9) to replace the variables $(\alpha,\beta)$ by the variables $(\xi,\phi)$ in Eq. (15), one obtains $$a(r,\theta) = \int_{\phi=0}^{2\pi} \int_{\xi=0}^{\infty} [q'(\alpha,\phi-\alpha) + q'(-\alpha,\phi+\alpha+\pi)] \quad (16)$$
$$h(r\cos(\phi-\theta)-\xi)d\xi d\phi.$$

Let $Q'_k(\alpha)$ denote the Fourier series expansion of the weighted fan-beam sinogram $q'(\alpha,\beta)$. Then $$Q'_k(\alpha) = \frac{1}{2\pi} \int_{\beta=0}^{2\pi} q(\alpha,\beta)\omega(\alpha,\beta) e^{-jk\beta} d\beta \text{ and} \quad (17)$$

$$q'(\alpha,\beta) = \sum_{k=-\infty}^{\infty} Q'_k(\alpha) e^{-jk\beta}.$$

Substituting Eq. (17) into Eq. (16) yields $$a(r,\theta) = \frac{1}{2} \int_{\phi=0}^{2\pi} \int_{\xi=0}^{\infty} \sum_{k=-\infty}^{\infty} [\gamma^k Q'_k(\alpha) + (-1)^k \gamma^{-k} Q'_k(-\alpha)] \quad (18)$$
$$e^{jk\phi} h(r\cos(\phi-\theta)-\xi)d\xi d\phi.$$

Comparison of Eqs. (7) and (18) indicates that $$P_k(\xi) = \frac{1}{2}[\gamma^k Q'_k(\alpha) + (-1)^k \gamma^{-k} Q'_k(-\alpha)]. \quad (19)$$

This is an important relationship that can be used to estimate $P_k(\xi)$ from the halfscan fan-beam sinogram. From this estimated $P_k(\xi)$, one can subsequently reconstruct the image by use of the FBP algorithm. Therefore, the combination of Eqs. (19) and (7) forms a halfscan-hybrid algorithm. Moreover, different choices of the weighting function $\omega(\alpha,\beta)$ yield different halfscan-hybrid algorithms that respond differently to the effects of data noise and sample aliasing.

The procedure of using the halfscan hybrid algorithms will be discussed in more detail next. As a first step a weighted fan-beam sinogram $q'(\alpha,\beta)$ is determined. Using the halfscan fan-beam sinogram $q(\alpha,\beta)$ and the selected weighting function $\omega(\alpha,\beta)$ in Eq. (13), one can readily obtain the weighted fan-beam sinogram $q'(\alpha,\beta)$.

Next a partial Fourier transform $Q'_k(\alpha)$ of the weighted sinogram $q'(\alpha,\beta)$ with respect to β is determined. One can obtain $Q'_k(\alpha)$ from $q'(\alpha,\beta)$, which is calculated in step (1), by performing a Fourier series expansion with respect to $\beta$ (see Eq. (17)).

Next a Fourier series expansion of the parallel beam sinogram $P_k(\xi)$ is determined. Using the calculated $Q'_k(\alpha)$ and $Q'_k(-\alpha)$ in Eq. (19), one can obtain $P_k(\xi)$. Due to the non-linear relationship between $\xi$ and $\alpha$ (see Eq. (9)), the desired points $\alpha$ at which $P_k(\xi)$ is to be calculated do not coincide, in general, with the values of $\alpha$ at which $Q'_k(\alpha)$ and $Q'_k(-\alpha)$ are sampled. However, $P_k(\xi)$ can be obtained by interpolation of the right side of Eq. (17) for each desired $\xi$ value. Because the sample density of $q(\alpha,\beta)$ in $\alpha$ is generally high, linear interpolation is usually sufficiently accurate.

Finally the image may be reconstructed. Applying the FBP algorithm in Eq. (7) to $P_k(\xi)$, which is estimated in step (3), one can reconstruct the image $a(r,\theta)$.

As with the halfscan-FFBP algorithms, the halfscan-hybrid algorithms use step (1) to generate the weighted fan-beam sinogram $q'(\alpha,\beta)$. However, the implementation steps (2)–(4) described above for the halfscan-hybrid algorithms are unique.

Figure 3A:
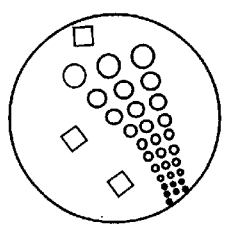
FIG. 3 depicts exemplary images produced by the system of FIG. 1.

The results of using halfscan hybrid algorithms will be discussed next. A 128×128 numerical phantom, as shown in FIG. 3a, was used in the simulation studies. This phantom consists of a set of square and circular structures with different sizes, orientations, and locations that are embedded in a circular disk background. A noiseless halfscan fan-beam sinogram that contains 92 projections was generated by use of this numerical phantom and an equiangular fan-beam configuration with a focal length F=91 pixels. These projections are uniformly sampled over 260°, each containing 128 bins that have the same size as that of the image pixels. The weighting function proposed by Crawford was used in the simulation studies and is given by $$\omega(\alpha,\beta)=3x^2(\alpha,\beta)-2x^3(\alpha,\beta). \quad (20)$$

where $$x(\alpha,\beta) = \frac{\beta}{2\alpha_m - 2\alpha}$$

for $(\alpha,\beta)$ in subspace A, and $$x(\alpha,\beta) = \frac{\pi + 2\alpha - \beta}{2\alpha_m + 2\alpha}$$

for $(\alpha,\beta)$ in subspace B. In an attempt to evaluate the noise level and uniformity in images reconstructed by use of the halfscan-FFBP and halfscan-hybrid algorithms, we generated noisy halfscan fan-beam sinograms that contain stationary white Gaussian noise, using the noiseless halfscan fan-beam sinogram as the mean. From these noisy sinograms noisy images were reconstructed by use of the halfscan-hybrid and halfscan-FFBP algorithms and subsequently empirical image variance was calculated.

Figure 3B:
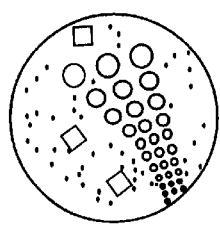
Figure 3C:
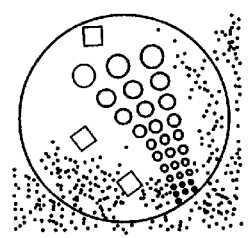
Figure 4A:
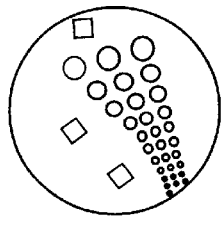
FIG. 4 depicts further exemplary images produced by the system of FIG. 1.
Figure 4B:
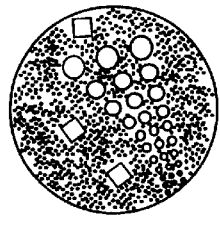
Figure 4C:
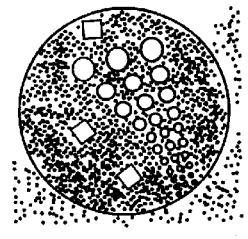

Reconstructed images in Halfscan CT will now be considered. The halfscan-hybrid and halfscan-FFBP algorithms were used to reconstruct images, which are shown in FIGS. 3b and 3c, respectively, from the noiseless halfscan sinogram. The evident artifacts in the outer region of the image in FIG. 3c suggest that the halfscan-FFBP algorithm is more susceptible to the effect of sample aliasing than is the halfscan-hybrid algorithm (see FIG. 3b). Similarly, from the simulated noisy sinogram, these two algorithms were used to reconstruct images that are shown in FIGS. 4b and 4c, respectively. Clearly, the noise levels in the outer regions of the image in FIG. 4c appear to be higher than are those in the outer regions of the image in FIG. 4b, confirming qualitatively that the halfscan-FFBP algorithm amplifies the effects of data noise and sample aliasing inherent in the noisy and discrete data more seriously than does the halfscan-hybrid algorithm.

Figure 5:
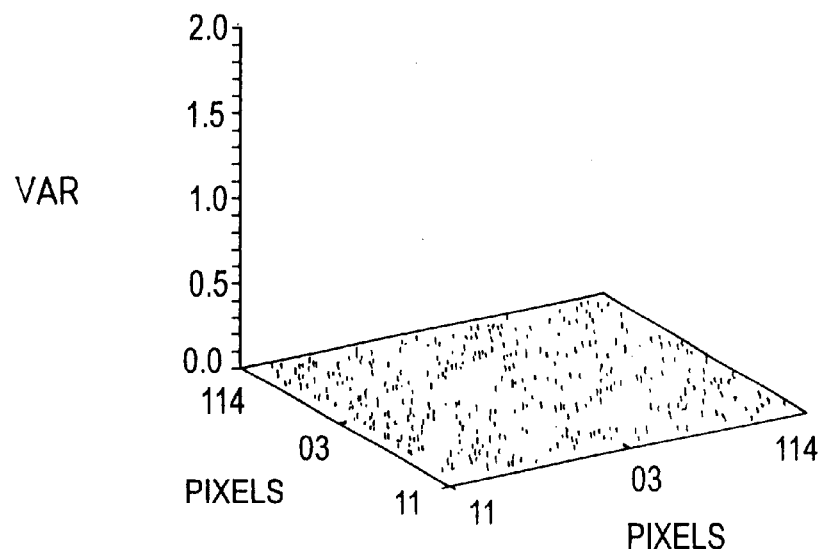
FIG. 5 depicts a surface plot of the image variance obtained with the halfscan algorithm of the system of FIG. 1.
Figure 6:
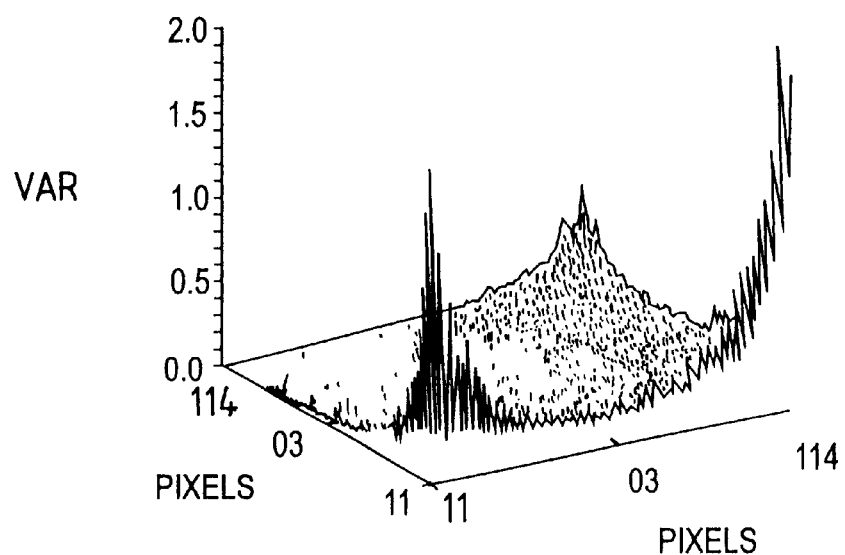
FIG. 6 depicts the image variance obtained with the halfscan-FFBP algorithm.
Figure 7A:
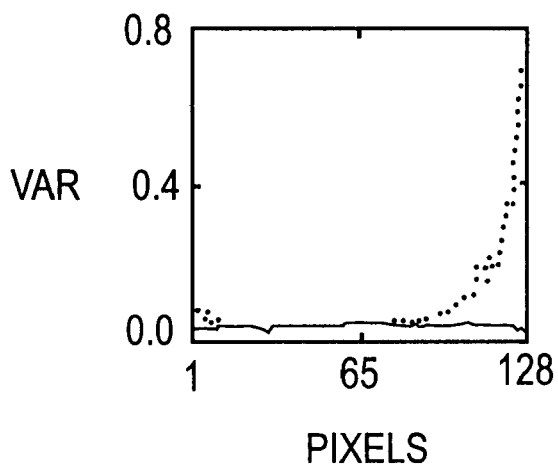
FIG. 7 depicts image variance along a horizontal line passing through a center of the image space of the system of FIG. 1.
Figure 7B:
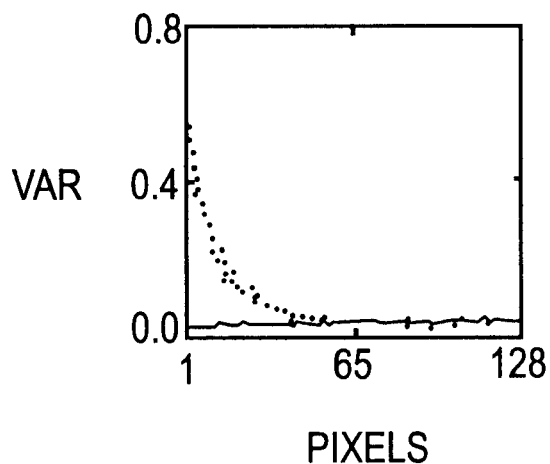

The noise properties of reconstructed images in halfscan CT will now be discussed. The noise properties of the images reconstructed by use of the halfscan-hybrid and halfscan-FFBP algorithms were quantitatively considered. Using 500 sets of simulated noisy halfscan sinograms, each of these two algorithms were employed to reconstruct 500 images and then the image variance was calculated empirically from these noisy images. In FIGS. 5 and 6, we show the surface plots of the image variance obtained by use of the halfscan-hybrid and halfscan-FFBP algorithms, respectively. These results indicate that the noise levels in images reconstructed by use of the halfscan-hybrid algorithm are much more uniform than are those in images reconstructed by use of the halfscan-FFBP algorithm. In an attempt to provide a quantitatively detailed comparison, we plot in FIGS. 7a and 7b the image variance along a horizontal line and a vertical line, respectively, that pass through the center of the image space. These results indicate quantitatively that the image variance obtained with the halfscan-hybrid algorithm is generally lower and more uniform than that obtained with the halfscan-FFBP algorithm. This result is consistent with those observed in the fullscan situation.

The non-symmetric noise properties of reconstructed images in Halfscan CT were considered. As analyzed by Pan in "OPTIMAL NOISE CONTROL AND FAST RECONSTRUCTION OF FAN-BEAM COMPUTED TOMOGRAPHIC IMAGE" (Med. Phys., 26, 689–697 (1999)), the high and non-uniform noise levels in images obtained with the FFBP algorithm are caused by the ratio of F/L, which can be larger than 1 for spatial locations in the outer region of the image and, thus, can amplify significantly the effects of data noise and sample aliasing inherent in the noisy and discrete data. However, the noise levels in images reconstructed by use of the FFBP algorithm from fullscan fan-beam sinograms appear qualitatively circularly symmetric around the center of the image space, whereas the noise levels in images reconstructed by use of the halfscan-FFBP algorithm from the halfscan fan-beam sinogram are highly non-symmetric, as shown in FIGS. 4c, 6, and 7. For example, in FIGS. 4c and 6, the noise levels in the upper left regions are much lower than are those in other outer regions of the image obtained with the halfscan-FFBP algorithm.

These observations can be understood as follows: As shown in Eq. (10), the filtered projections (i.e., the integration over $\alpha$ in Eq. (10)) are multiplied by the ratio of $(F/L)^2$ before being backprojected into the image space. For a given projection angle $\beta$, the ratio of F/L (see its expression below Eq. (10)) can be smaller or larger than 1, depending upon whether the locations $(r,\theta)$ in the image space are close to or far away from the detector array that acquires the projections at angle $\beta$. Therefore, when the filtered projections are backprojected into the image space, the factor $L^{-2}$ suppresses or amplifies the effects of data noise and sample aliasing, depending on whether the locations in the image space that are close to or far away from the detector array at angle β. In a fullscan situation, the projections and, thus, the corresponding filtered projections can be obtained for $0 \leq \beta \leq 2\pi$. When the products of $(F/L)^2$ and the filtered projections are backprojected into the image space for all projection angles between 0 and π, the image noise levels are non-uniform (e.g., they increase as r increase), but are qualitatively circularly symmetric about the center of the image space. However, in a halfscan situation, projections are not acquired at certain angles β. For example, our simulated halfscan sinogram contains no projections for angles around the lower right corner the image space in FIG. 4c. These zero-projection views contribute no values to the reconstructed image, and, therefore, the image regions which are close to and far away from the zero-projection views contain contributions mainly from projection views conjugate to the zero-projection views. Therefore, noise levels in these image regions are either higher or lower than those in the center of the image space, respectively. In our simulation studies, the zero-projection views are around the lower right corner of the image space (see FIG. 4c), and their conjugate projection views are around the upper left corner of the image space. Therefore, the noise levels in the lower right and upper left regions in the image space are higher and lower, respectively, than those in the center of the image space. This observation can readily be confirmed by the result in FIG. 6.

The hybrid algorithms discussed herein are superior to the FFBP algorithm in terms of computational efficiency and noise amplification. However, these hybrid algorithms cannot be applied directly to the halfscan fan-beam sinogram because they involve the calculation of the Fourier series expansion of the fullscan fan-beam sinogram, which is not available in the halfscan situation. In this work, the halfscan-hybrid algorithms are developed for image reconstruction in halfscan CT. The key is that the weighted $q'(\alpha,\beta)$ can be treated as a "fullscan fan-beam sinogram," and one can use its Fourier series expansion to estimate the parallel-beam sinogram without invoking an explicit interpolation between the parallel-beam and fan-beam projection angles. Different hybrid algorithms exploit the redundant information in a fullscan fan-beam sinogram by using different combination coefficients ω in Eq. (12). However, as shown in Eq. (19), different halfscan-hybrid algorithms use the same combination coefficient ω=½, and, instead, they exploit the partially redundant information in a halfscan fan-beam sinogram by using different weighting functions, as shown in Eq. (13).

Numerical evaluation indicates that the halfscan-hybrid algorithms are computationally more efficient than is the currently used halfscan-FFBP algorithm. Such a computational advantage may become more significant for the reconstruction task in single- and multi-slice helical CT, which generally reconstructs a large number of images of large size. More importantly, the results of our simulation studies demonstrated clearly that the noise levels in images reconstructed by use of the halfscan-hybrid algorithm are generally lower and spatially much more uniform than are those in images reconstructed by use of the halfscan-FFBP algorithm. Such a reduction and uniformity of image noise levels may be translated into improvement of the accuracy and precision of lesion detection and parameter estimation in noisy CT images without increasing the radiation dose to the patient. On the other hand, because the noise levels (i.e., image variance) in quantum limited CT are generally related to the reciprocals of radiation exposures to the patient, to reconstruct images with comparable noise levels, the halfscan-hybrid algorithm requires a lower radiation dose (i.e., a smaller number of X-rays) than does the halfscan-FFBP algorithm. Again, this advantage of the halfscan-hybrid algorithms over the halfscan-FFBP algorithm can become cumulatively significant in single- and multi-slice helical CT, in which the imaging of multiple slices generally requires high radiation dose. Finally, the results in this work can be generalized to other fan-beam imaging modalities such as single-photonemission computed tomography with different fan-beam projection configurations.

A specific embodiment of a method and apparatus for creating CT images according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method of reconstructing a tomographic image from a halfscan fan-beam sinogram using the parallel beam reconstruction algorithms, such method comprising the steps of:

weighting at least some elements of the halfscan fan-beam sinogram to a weighted fan-beam sinogram;

expanding the weighted fan-beam sinogram into a Fourier series;

linearly interpolating at least some elements of the Fourier series to form a parallel beam sinogram of linearly interpolated data; and reconstructing the image from the parallel beam sinogram using the parallel beam reconstruction algorithms.

2. The method of reconstructing a tomographic image as in claim 1 wherein the step of reconstructing the image from the parallel beam sinogram further comprises performing an inverse Fourier transform on the linearly interpolated data.

3. The method of reconstructing a tomographic image as in claim 1 wherein the step of expanding the weighted fan-beam sinogram into a Fourier series further comprises performing a fast Fourier transform on data elements, $q(\alpha, \beta)$, of the halfscan fan-beam sinogram with respect to a set of projection angles, β.

4. The method of reconstructing a tomographic image as in claim 3 further comprising forming a linear combination of complementary data elements of the transformed data, lying at projection bin α and −α.

5. The method of reconstructing a tomographic image as in claim 4 wherein the step of linearly interpolating further comprises forming a regularly spaced set of data, $P_k(\xi)$, in Fourier space.

6. The method of reconstructing a tomographic image as in claim 5 wherein the step of forming a regularly spaced set of data, $P_k(\xi)$, in Fourier space further comprises selecting a projection angle, $\phi_1$, and an offset distance, $\xi_1$, in a parallel beam sinogram coordinate space.

7. The method of reconstructing a tomographic image as in claim 6 further comprising determining a projection angle, $\beta_1$, of the halfscan fan-beam sinogram which corresponds to the selected projection angle, $\phi_1$.

8. The method of reconstructing a tomographic image as in claim 7 wherein the step of linearly interpolating the linear combination further comprises determining a set of offset angles, $\alpha_1$, and associated pair of data elements of the halfscan fan-beam sinogram which correspond to the determined projection angle and the offset distance $\xi_1$.

9. The method of reconstructing a tomographic image as in claim 8 further comprising calculating a pair of fan beam offset distances, $\xi_{fb1}$, $\xi_{fb2}$, for the set of offset angles, $\alpha_1$.

10. The method of reconstructing a tomographic image as in claim 9 further comprising linearly interpolating a data element of the regularly spaced set of data at projection angle $\phi_1$ and offset distance $\xi_1$ based on the pair of data elements at offset distances $\xi_{fb1}$ and $\xi_{fb2}$.

11. An apparatus for reconstructing a tomographic image from a halfscan fan-beam sinogram using the parallel beam reconstruction algorithms, such apparatus comprising:

means for weighting at least some elements of the halfscan fan-beam sinogram to form a weighted fan-beam sinogram;

means for expanding the weighted fan-beam sinogram into a Fourier series;

means for linearly interpolating at least some elements of the Fourier series to form a parallel beam sinogram of linearly interpolated data; and means for reconstructing the image from the parallel beam sinogram using the parallel beam reconstruction algorithms.

12. The apparatus for reconstructing a tomographic image as in claim 11 wherein the means for reconstructing the image from the parallel beam sinogram further comprises means for performing an inverse Fourier transform on the linearly interpolated data.

13. The apparatus for reconstructing a tomographic image as in claim 11 wherein the means for expanding the weighted fan-beam sinogram into a Fourier series further comprises means for performing a fast Fourier transform on data elements, $q(\alpha,\beta)$, of the halfscan fan-beam sinogram with respect to a set of projection angles, $\alpha$.

14. The apparatus for reconstructing a tomographic image as in claim 13 further comprising means for forming a linear combination of complementary data elements of the transformed data, lying at projection bin $\alpha$ and $-\alpha$.

15. The apparatus for reconstructing a tomographic image as in claim 14 wherein the means for linearly interpolating further comprises means for forming a regularly spaced set of data, $P_k(\xi)$, in Fourier space.

16. The apparatus for reconstructing a tomographic image as in claim 15 wherein the means for forming a regularly spaced set of data, $P_k(\xi)$, in Fourier space further comprises means for selecting a projection angle, $\phi_1$, and an offset distance, $\xi_1$, in a parallel beam sinogram coordinate space.

17. The apparatus for reconstructing a tomographic image as in claim 16 further comprising means for determining a projection angle, $\beta_1$, of the halfscan fan-beam sinogram which corresponds to the selected projection angle, $\phi_1$.

18. The apparatus for reconstructing a tomographic image as in claim 17 wherein the means for linearly interpolating the linear combination further comprises means for determining a set of offset angles, $\alpha_1$, and associated pair of data elements of the halfscan fan-beam sinogram which correspond to the determined projection angle, $\beta_1$, and the offset distance $\xi_1$.

19. The apparatus for reconstructing a tomographic image as in claim 18 further comprising means for calculating a pair of fan beam offset distances, $\xi_{fb1}$, $\xi_{fb2}$, for the set of offset angles, $\alpha_1$.

20. The apparatus for reconstructing a tomographic image as in claim 19 further comprising means for linearly interpolating a data element of the regularly spaced set of data at projection angle $\phi_1$ and offset distance $\xi_1$ based the pair of data elements at offset distances $\xi_{fb1}$ and $\xi_{fb2}$.

21. An apparatus for reconstructing a tomographic image from a halfscan fan-beam sinogram using the parallel beam reconstruction algorithms, such apparatus comprising:

a weighting processor adapted to weight at least some elements of the halfscan fan-beam sinogram to form a weighted fan-beam sinogram;

an expansion processor adapted to expand the weighted fan-beam sinogram into a Fourier series;

an interpolation processor adapted to linearly interpolating at least some elements of the Fourier series to form a parallel beam sinogram of linearly interpolated data; and a reconstruction processor adapted to reconstruct the image from the parallel beam sinogram using the parallel beam reconstruction algorithms.

22. The apparatus for reconstructing a tomographic image as in claim 21 wherein the reconstruction processor further comprises a Fourier processor adapted to perform an inverse Fourier transform on the linearly interpolated data.

23. A method of reconstructing an tomographic image from a halfscan fan-beam sinogram using the parallel beam reconstruction algorithms, such method comprising the steps of:

forming a weighted fan-beam sinogram from the halfscan fan-beam sinogram;

forming a Fourier series expansion of the weighted fan-beam sinogram;

linearly interpolating the Fourier series expansion to form a parallel beam sinogram; and reconstructing the image using the parallel beam reconstruction algorithms.

24. A method of reconstructing a tomographic image using the parallel beam reconstruction algorithms and a halfscan fan-beam sinogram, such method comprising the steps of:

obtaining a weighted fan-beam sinogram, $q(\alpha,\beta)$, from the halfscan fan-beam sinogram, $q(\alpha,\beta)$, and a selected weighting function, $\omega(\alpha,\beta)$;

performing a Fourier series expansion of the weighted fan-beam sinogram, $q(\alpha,\beta)$, with respect to a set of projection angles, $\beta$;

linearly interpolating the Fourier expanded sinogram to obtain a regularly spaced set of data, $P_k(\xi)$, in Fourier space;

reconstructing an image, $a(r,\upsilon)$ using the linearly interpolated data.

25. The method of reconstructing a tomographic image as in claim 24 wherein the step of linearly interpolating further comprises forming a linear combination of data elements of the transformed data, lying at projection bin locations $\alpha$ and $-\alpha$.

* * * * *